United States Patent
Suzuki et al.

(10) Patent No.: US 10,058,238 B2
(45) Date of Patent: Aug. 28, 2018

(54) VIDEO OUTPUT APPARATUS

(71) Applicant: OLYMPUS CORPORATION, Tokyo (JP)

(72) Inventors: Tatsuhiko Suzuki, Hino (JP); Takehiko Ito, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 218 days.

(21) Appl. No.: 15/220,452

(22) Filed: Jul. 27, 2016

(65) Prior Publication Data

US 2016/0331215 A1 Nov. 17, 2016

Related U.S. Application Data

(63) Continuation of application No. PCT/JP2015/051092, filed on Jan. 16, 2015.

(30) Foreign Application Priority Data

Jan. 29, 2014 (JP) .................................. 2014-014682

(51) Int. Cl.
*A61B 1/04* (2006.01)
*H04N 5/265* (2006.01)
(Continued)

(52) U.S. Cl.
CPC ............. *A61B 1/04* (2013.01); *A61B 1/00009* (2013.01); *G02B 23/2484* (2013.01); *H04N 5/265* (2013.01); *H04N 7/18* (2013.01)

(58) Field of Classification Search
CPC ........ A61B 1/04; H04N 5/265; G02B 23/2484
See application file for complete search history.

(56) References Cited

U.S. PATENT DOCUMENTS

2008/0284910 A1\* 11/2008 Erskine .................. G11B 27/11
348/468
2009/0027490 A1 1/2009 Hirai et al.

FOREIGN PATENT DOCUMENTS

EP 1 779 766 A1 5/2007
EP 1889564 A1 2/2008
(Continued)

OTHER PUBLICATIONS

International Search Report dated Apr. 21, 2015 issued in PCT/JP2015/051092.

(Continued)

*Primary Examiner* — Nam Pham
(74) *Attorney, Agent, or Firm* — Scully, Scott, Murphy & Presser, P.C.

(57) ABSTRACT

A video output apparatus includes: a video signal processing section that generates a first video signal having a first resolution; a first text superimposing section that superimposes first textual information on the first video signal; a first output section that outputs the first video signal with the first textual information superimposed; a reduction processing section that receives the first video signal and generates a second video signal having a second resolution that is lower than the first resolution; a second text superimposing section that superimposes second textual information on the second video signal; and a second output section that outputs the second video signal with the second textual information superimposed.

5 Claims, 6 Drawing Sheets

(51) Int. Cl.
*H04N 7/18* (2006.01)
*A61B 1/00* (2006.01)
*G02B 23/24* (2006.01)

(56) References Cited

FOREIGN PATENT DOCUMENTS

| | | |
|---|---|---|
| JP | H11-341484 A | 12/1999 |
| JP | 2006-334323 A | 12/2006 |
| JP | 2007-216021 A | 8/2007 |
| WO | 2006/132154 A1 | 12/2006 |

OTHER PUBLICATIONS

Extended Supplementary European Search Report dated Oct. 13, 2017 received in 15743599.1.

* cited by examiner

FIG. 4

| · PATIENT DATA | OFF |
|---|---|
| · CLOCK INFORMATION | ON |
| · IMAGE RECORDING APPARATUS INFORMATION | OFF |
| · REMAINING MEMORY CAPACITY | OFF |
| · IMAGE INFORMATION | ON |
| · PREDETERMINED COMMENT | ON |
| · PIP IMAGE | ON |
| · POP IMAGE | OFF |
| · INDEX IMAGE | OFF |
| · ARROW POINTER | OFF |
| · STATUS ICON | OFF |

VIDEO OUTPUT APPARATUS

CROSS REFERENCE TO RELATED APPLICATION

This application is a continuation application of PCT/JP2015/051092 filed on Jan. 16, 2015 and claims benefit of Japanese Application No. 2014-014682 filed in Japan on Jan. 29, 2014, the entire contents of which are incorporated herein by this reference.

BACKGROUND OF INVENTION

1. Field of the Invention

The present invention relates to a video output apparatus that subjects an image pickup signal to predetermined processing and thereby generates and outputs a video signal.

2. Description of the Related Art

Conventionally, in a medical field and an industrial field, endoscopes including an image pickup device have been widely used. Also, a technique that provides an endoscope system in which a signal processing apparatus called a processor, which is detachably connected to an endoscope, performs various signal processing relating to the endoscope has been known.

Also, as the aforementioned signal processing apparatus, for example, Japanese Patent Application Laid-Open Publication No. 2006-334323 discloses a digital image recording apparatus that subjects an image pickup signal obtained by picking up a subject image to predetermined processing to generate a video signal and outputs the video signal to a display apparatus such as a monitor or a recording device that can record the video signal.

The digital image recording apparatus described in Japanese Patent Application Laid-Open Publication No. 2006-334323 is a recording device that can record image data representing information that is the same as that of an image (endoscopic image plus additional information such as textual information) displayed on a monitor, and enables whether or not the additional information is displayed to be set for each item when image data recorded in the recording apparatus is viewed.

Also, Japanese Patent Application Laid-Open Publication No. 2006-334323 discloses a technique that records data representing an endoscopic screen displayed on the monitor, into an external recording device, and enables whether or not display of additional information added to the endoscopic image is necessary to be set for each item when the image data recorded in the external recording device is reproduced and viewed.

SUMMARY OF THE INVENTION

A video output apparatus according to an aspect of the present invention includes: a video signal processing section that subjects an image pickup signal obtained by picking up an image of a subject to image processing to generate a first video signal representing an image having a first resolution; a first text superimposing section that superimposes first textual information on the first video signal; a first output section that outputs the first video signal with the first textual information superimposed; a reduction processing section that receives the first video signal outputted from the video signal processing section, and subjects the received video signal to reduction processing to generate a second video signal representing an image having a second resolution that is lower than the first resolution; a second text superimposing section that superimposes second textual information on the second video signal; and a second output section that outputs the second video signal with the second textual information superimposed.

BRIEF DESCRIPTION OF THE DRAWINGS

FIG. 4 is a chart indicating a correspondence between textual information types and ON/OFF settings in the video output apparatus according to the first embodiment;

DETAILED DESCRIPTION OF THE PREFERRED EMBODIMENT(S)

Embodiments of the present invention will be described with reference to the drawings.

First Embodiment

Figure 1:
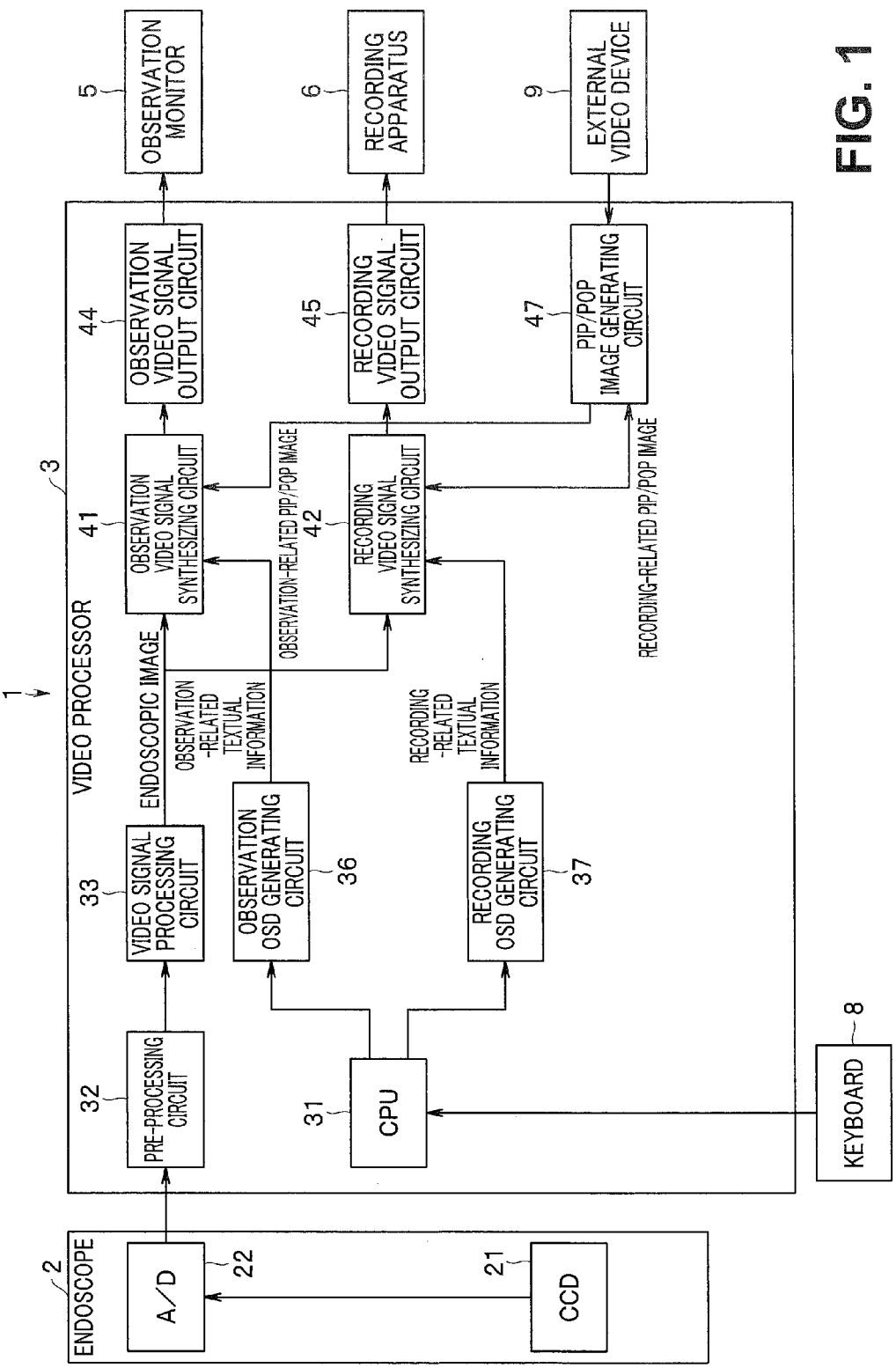
FIG. 1 is a diagram illustrating a configuration of a video output apparatus according to a first embodiment of the present invention.

As illustrated in FIG. 1 an endoscope system 1 according to a first embodiment of the present invention mainly includes: an endoscope 2 including a CCD image sensor 21 that is provided at a distal end of an insertion portion to be inserted into a subject and picks up an optical image of the subject and outputs a predetermined image pickup signal; a video processor 3, which is a signal processing apparatus that performs predetermined signal processing of the image pickup signal from the CCD image sensor 21; an observation monitor 5 that displays the predetermined video signal from the video processor 3; a recording apparatus 6 that records the predetermined video signal generated in the video processor 3, and a keyboard 8, via which predetermined operation is performed, the keyboard 8 being connected to the video processor 3.

The endoscope 2 includes an A/D conversion 22 that subjects an image pickup signal relating to a subject image outputted from the CCD image sensor 21 to predetermined A/D conversion and sends the resulting signal out to the video processor 3.

The video processor 3 includes: a CPU 31 that controls various circuits inside the video processor 3; a pre-processing circuit 32 that subjects an image pickup signal outputted from the CCD image sensor 21 to known pre-processing; and a video signal processing circuit 33 that subjects the signal processed in the pre-processing circuit 32 to predetermined image processing to generate a video signal, which is an endoscopic image signal, and outputs the video signal.

Here, the video processor 3 in the present embodiment is configured so as to generate an image pickup signal of an image of a subject picked up by the endoscope 2, associated with additional information relating to the subject.

Figure 2:
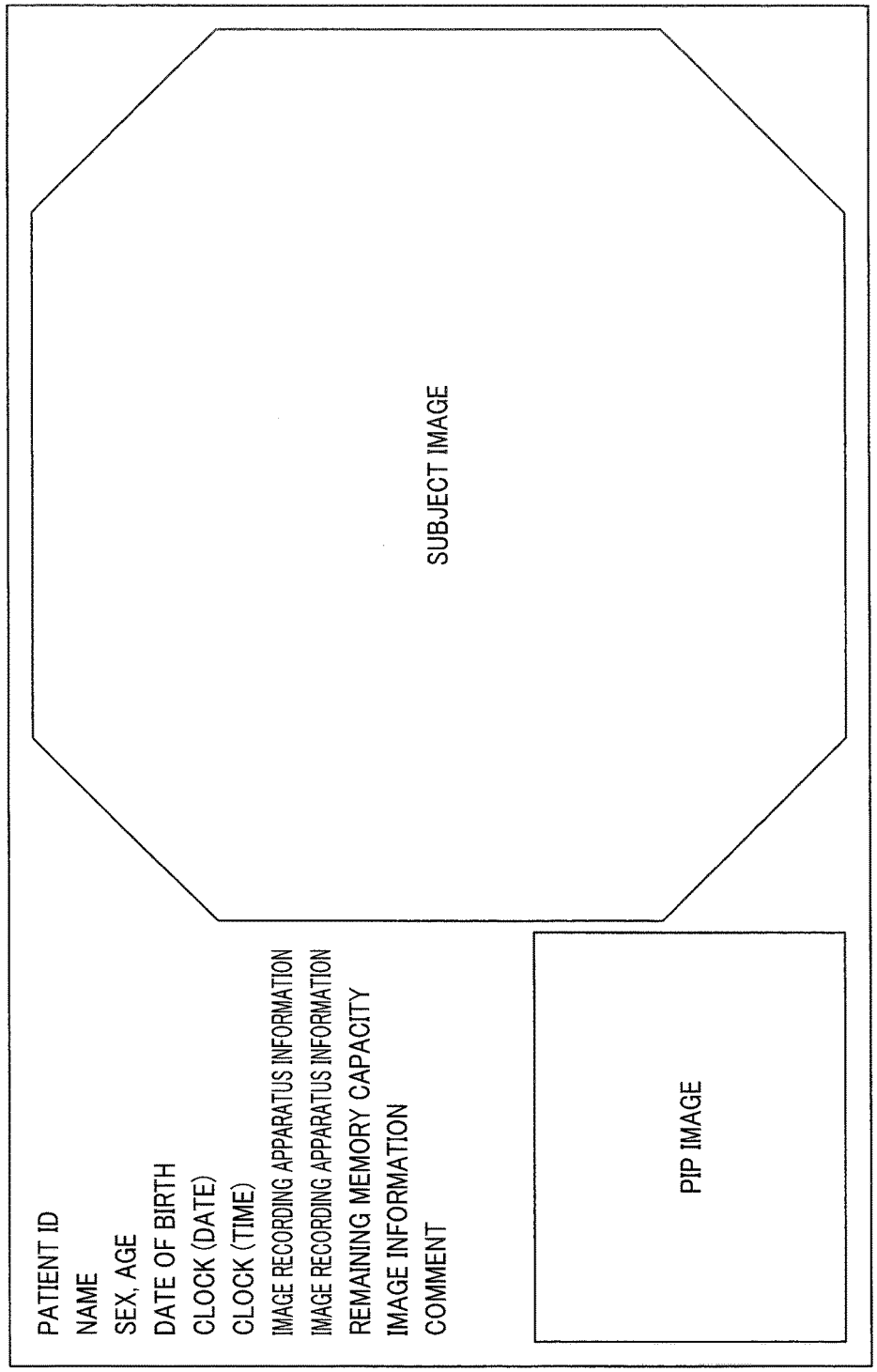
FIG. 2 is a diagram illustrating a display screen according to an observation video output signal in the video output apparatus according to the first embodiment.

More specifically, as illustrated in FIG. 2, the present embodiment is configured so that on a same screen displaying an image of a subject, predetermined additional information relating to the subject is displayed in the form of on-screen display (hereinafter referred to as "OSD").

Furthermore, the present embodiment is configured so that independent additional information, that is, observation additional information or recording additional information is provided to a video signal to be displayed on the observation monitor 5 and a video signal to be recorded into the recording apparatus 6, respectively, to generate new video signals that are independent from each other.

More specifically, the video processor 3 includes an observation OSD generating circuit 36 that, under the control of the CPU 31, generates observation OSD (observation additional information) to be displayed on the observation monitor 5, according to operation of the keyboard 8, and a recording OSD generating circuit 37 that, also under the control of the CPU 31, generates recording OSD (recording additional information) to be recorded into the recording apparatus 6, according to operation of the keyboard 8.

Observation-related textual information is outputted as OSD from the observation OSD generating circuit 36, and recording-related textual information is outputted as OSD from the recording OSD generating circuit 37. Note that, as described above, in the present embodiment, the observation-related textual information and the recording-related textual information are independent from each other.

In the present embodiment, for the observation-related textual information or recording-related textual information, which is OSD, for example, items illustrated in FIG. 4 are employed.

Furthermore, as illustrated in FIG. 4, under the control of the CPU 31, setting of items of the observation-related textual information and setting of items of the recording-related textual information (setting of additional information) can be made independently from each other according to operation of the keyboard 8.

Referring back to FIG. 1, the video processor 3 includes an observation video signal synthesizing circuit 41 for providing the observation OSD to a video signal, which is an endoscopic image signal outputted from the video signal processing circuit 33, that is, synthesizing the video signal and the observation OSD to generate an observation video signal, and outputting the observation video signal to the observation monitor 5.

The video processor 3 further includes a recording video signal synthesizing circuit 42 for providing the recording OSD to a video signal outputted from the video signal processing circuit 33, that is, synthesizing the video signal and the recording OSD to generate a recording video signal and outputting the recording video signal to the recording apparatus 6.

Also, the video processor 3 includes a PIP/POP image generating circuit 47 that generates a PIP/POP image relating to a video signal inputted from an external video device 9.

From the PIP/POP image generating circuit 47, an observation-related PIP/POP image or a recording-related PIP/POP image is outputted to the observation video signal synthesizing circuit 41 or the recording video signal synthesizing circuit 42, respectively.

The observation video signal synthesizing circuit 41 and the recording video signal synthesizing circuit 42 are configured so as to synthesize the observation-related PIP/POP image or the recording-related PIP/POP image from the PIP/POP image generating circuit 47 with a video signal, respectively.

Furthermore, the video processor 3 includes: an observation video signal output circuit 44 that outputs an observation video signal outputted from the observation video signal synthesizing circuit 41, to the observation monitor 5; and a recording video signal output circuit 45 that outputs a recording video signal outputted from the recording video signal synthesizing circuit 42, to the recording apparatus 6.

Next, operation of the first embodiment will be described.

Under the control of the CPU 31 in the video processor 3, the observation OSD generating circuit 36 and the recording OSD generating circuit 37 output observation-related textual information or recording-related textual information relating to the respective items, ON/OFF of which is set, for example, as illustrated in FIG. 4 via operation of the keyboard 8, to the observation video signal synthesizing circuit 41 or the recording video signal synthesizing circuit 42.

Next, under the control of the CPU 31, the observation video signal synthesizing circuit 41 provides observation-related textual information, which is observation OSD, to a video signal, which is an endoscopic image signal outputted from the video signal processing circuit 33, that is, synthesizes the video signal and the observation-related textual information to generate an observation video signal and outputs the observation video signal to the observation monitor 5 via the observation video signal output circuit 44 (see FIG. 2).

Here, if an observation-related PIP/POP image from the PIP/POP image generating circuit 47 is inputted to the observation video signal synthesizing circuit 41, the observation-related PIP/POP image is synthesized with the video signal (see FIG. 2).

Figure 3:
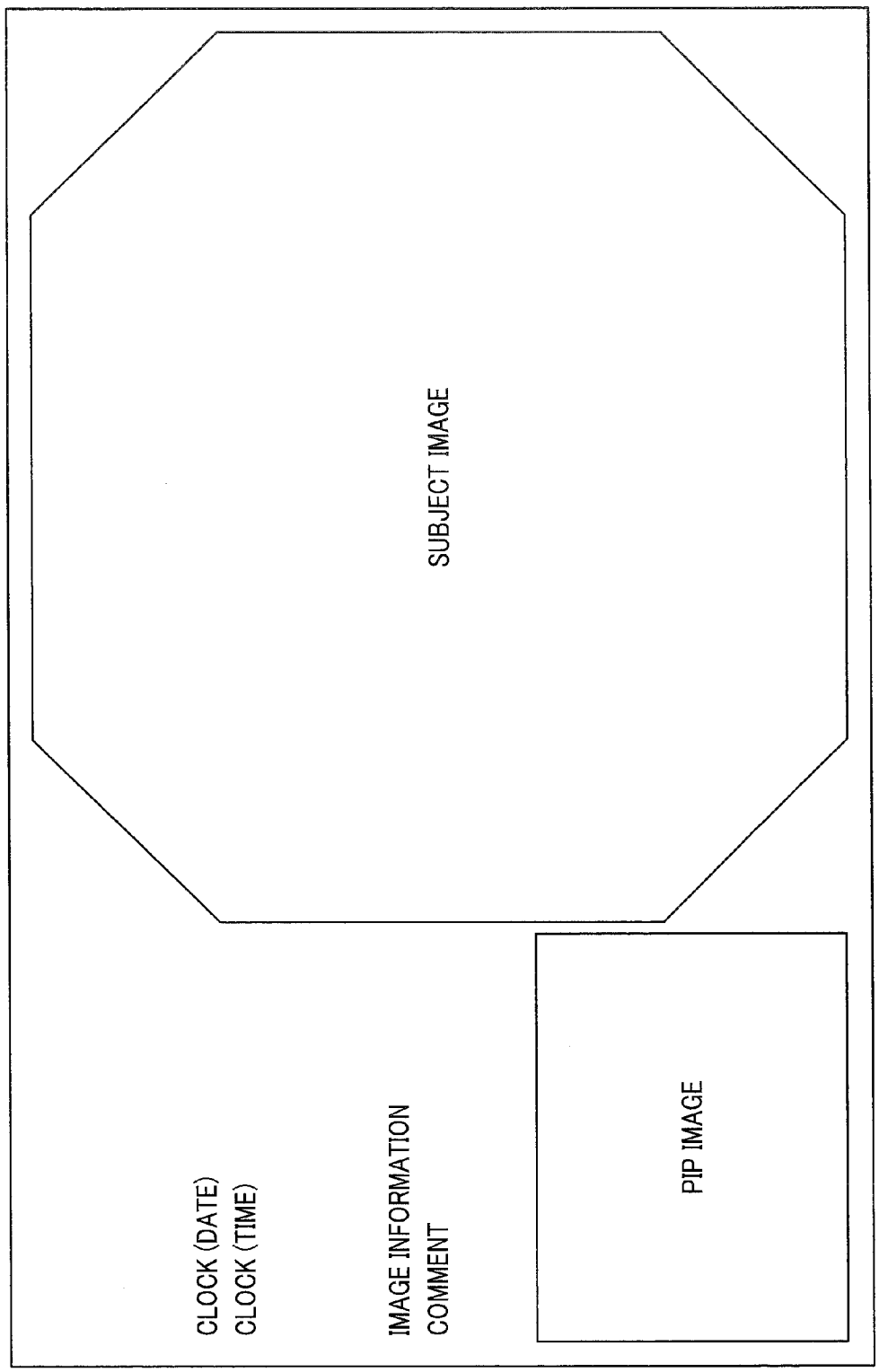
FIG. 3 is a diagram illustrating a display screen according to a recording video output signal in the video output apparatus according to the first embodiment.

On the other hand, under the control of the CPU 31, the recording video signal synthesizing circuit 42 provides recording-related textual information, which is recording OSD, to a video signal outputted from the video signal processing circuit 33, that is, synthesizes the video signal and the recording-related textual information to generate a recording video signal and outputs the recording video signal to the recording apparatus 6 via the recording video signal output circuit 45 (see FIG. 3).

Here, if a recording-related PIP/POP image from the PIP/POP image generating circuit 47 is inputted to the recording video signal synthesizing circuit 42, the recording-related PIP/POP image is synthesized with the video signal (see FIG. 3).

As described above, according to the first embodiment of the present invention, an observation video signal of a display screen of a subject image with additional information for observation display provided thereto, and a recording video signal of the display screen of the subject image with additional information for recording provided thereto can be generated independently from each other, and thus, for example, setting can be made so that patient data that is personal information to be displayed on the observation monitor 5 is prevented from being recorded.

Furthermore, the first embodiment of the present invention enables arbitrary setting of additional information relating to a recording video signal.

Second Embodiment

In recent years, as medical observation monitors, monitors that support so-called HDTV (high-definition television) are mainstream; however, as recording apparatuses to be connected to video processors in endoscope systems, so-called SDTV (standard definition television)-only devices, which do not support HDTV are still often used.

As described above, although in the first embodiment of the invention of the present application, mutually independent video signals are generated for an observation monitor and a recording apparatus, in a second embodiment of the invention of the present application, in view of the aforementioned monitor use status, a recording video signal that is independent from that for an observation monitor is generated not only for a recording apparatus that supports HDTV but also a recording apparatus that supports SDTV.

Figure 5:
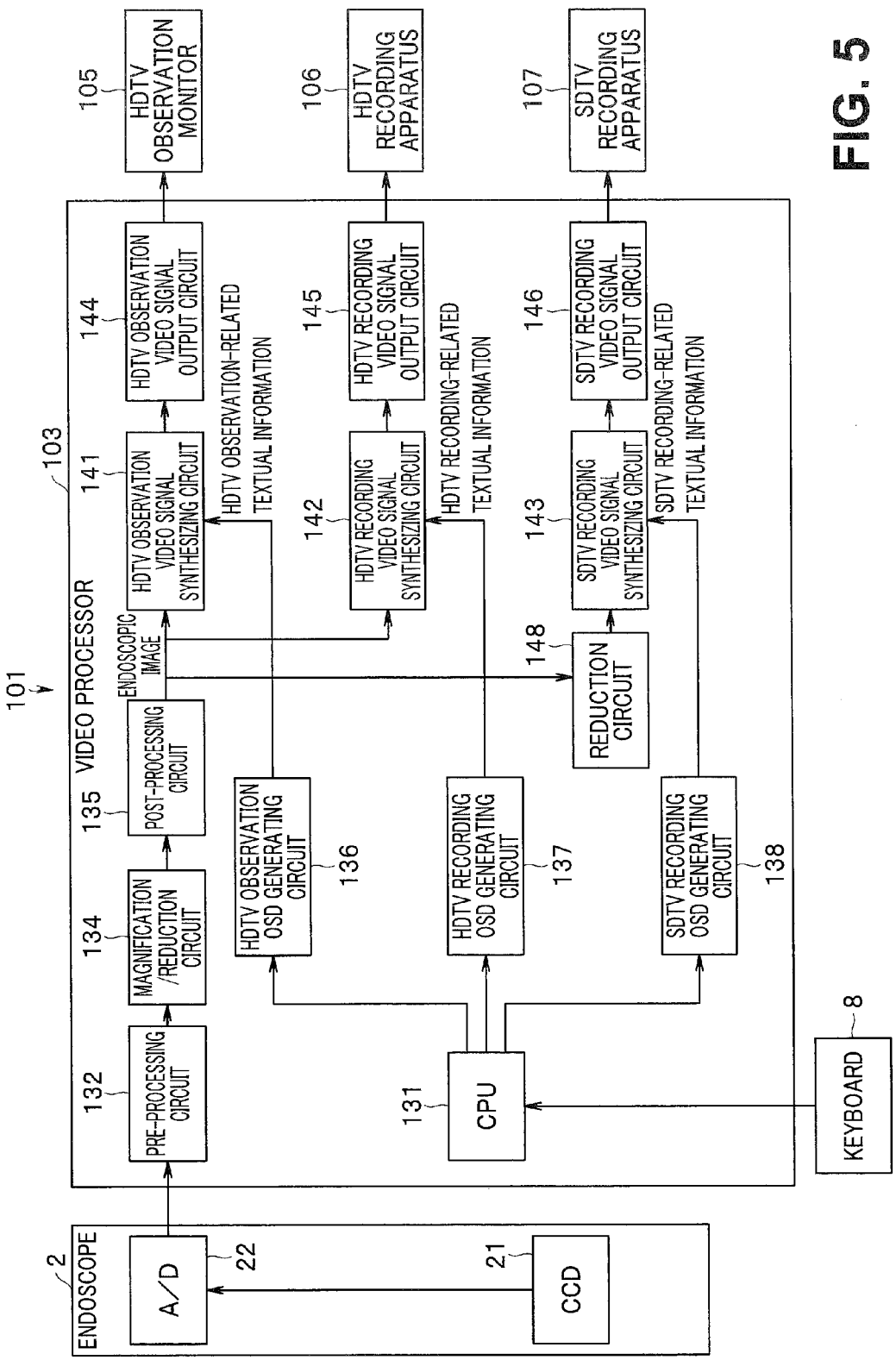
FIG. 5 is a diagram illustrating a configuration of a video output apparatus according to a second embodiment of the present invention.

FIG. 5 is a diagram illustrating a configuration of a video output apparatus according to a second embodiment of the present invention.

As illustrated in FIG. 5, as in the first embodiment, an endoscope system 101 according to the second embodiment of the present invention includes an endoscope 2 including a CCD image sensor 21, and a video processor 103 connected to the endoscope 2, the video processor 103 performing predetermined signal processing of an image pickup signal from the CCD image sensor 21 and generating a video signal that is independent from that for an observation monitor, for a recording apparatus that supports SDTV.

Furthermore, the endoscope system 101 mainly includes an HDTV observation monitor 105 that supports HDTV and displays a predetermined video signal from the video processor 103, an HDTV recording apparatus 106 that records a recording video signal for HDTV generated in the video processor 103, the video signal being independent from that for an observation monitor, an SDTV recording apparatus 107 that records a recording video signal for SDTV also generated in the video processor 103, the video signal being independent from that for an observation monitor, and a keyboard 8 via which predetermined operation is performed, the keyboard 8 being connected to the video processor 103.

As in the first embodiment, the endoscope 2 includes an A/D conversion 22 that subjects an image pickup signal relating to a subject image outputted from the CCD image sensor 21 to predetermined A/D conversion and sends the resulting signal out to the video processor 3.

In the second embodiment, the video processor 103 includes a CPU 131 that controls various circuits inside the video processor 103; a pre-processing circuit 132 that subjects an image pickup signal outputted from the CCD image sensor 21 to known pre-processing; a magnification/reduction circuit 134 that subjects the signal processed in the pre-processing circuit 32 to predetermined image processing to generate a video signal for HDTV; and a post-processing circuit 135 that subjects the signal processed in the magnification/reduction circuit 134 to known post-processing to generate a video signal, which is a predetermined endoscopic image signal and outputs the video signal.

The video processor 103 further includes a reduction circuit 148 that subjects the HDTV video signal outputted from the post-processing circuit 135, to predetermined reduction processing to generate an SDTV video signal and outputs the SDTV video signal.

As in the first embodiment, the video processor 103 in the second embodiment is also configured so as to generate an image pickup signal of a subject image picked up by the endoscope 2, associated with additional information relating to the subject. In other words, the present embodiment is also configured so that on a same screen displaying a subject image, predetermined additional information relating to the subject is displayed in the form of OSD.

The video processor 103 further includes: an HDTV observation OSD generating circuit 136 that, under the control of the CPU 131, generates observation OSD (observation additional information) to be displayed on the HDTV observation monitor 105 according to operation of the keyboard 8; an HDTV recording OSD generating circuit 137 that generates recording OSD (recording additional information) to be recorded into the HDTV recording apparatus 106, in the same manner as above; and a SDTV recording OSD generating circuit 138 that generates recording OSD to be recorded into the SDTV recording apparatus 107, in the same manner as above.

HDTV observation-related textual information is outputted as OSD from the HDTV observation OSD generating circuit 136, HDTV recording-related textual information is outputted as OSD from the HDTV recording OSD generating circuit 137, and SDTV recording-related textual information is outputted as OSD from the SDTV recording OSD generating circuit 138.

Note that, as described above, in the second embodiment, also, the HDTV observation-related textual information, the HDTV recording-related textual information and the SDTV recording-related textual information are independent from one another.

As in the first embodiment, in the second embodiment, also, for the HDTV observation-related textual information, the HDTV recording-related textual information or the SDTV recording-related textual information, which is the OSD, the items illustrated in FIG. 4 are employed, and furthermore, as illustrated in FIG. 4, under the control of the CPU 31, setting of items of the observation-related textual information and setting of items of the recording-related textual information (setting of additional information) can be made independently from each other according to operation of the keyboard 8.

Referring back to FIG. 5, the video processor 103 includes an HDTV observation video signal synthesizing circuit 141 for providing the HDTV observation OSD (HDTV observation-related textual information) to an HDTV video signal, which is an endoscopic image signal outputted from the post-processing circuit 135, that is, synthesizing the HDTV video signal and the HDTV observation OSD to generate an HDTV observation video signal and outputting the HDTV observation video signal to the HDTV observation monitor 105.

Also, the video processor 103 includes an HDTV recording video signal synthesizing circuit 142 for providing the HDTV recording OSD (HDTV recording-related textual information) to an HDTV video signal outputted from the post-processing circuit 135, that is, synthesizing the HDTV video signal and the HDTV recording OSD to generate an HDTV recording video signal and outputting the HDTV recording video signal to the HDTV recording apparatus 106.

The video processor 103 further includes an SDTV recording video signal synthesizing circuit 143 for providing the SDTV recording OSD (SDTV recording-related textual information) to an SDTV video signal from the reduction circuit 148 that subjects an HDTV video signal outputted from the post-processing circuit 135 to predetermined reduction processing, that is, synthesizing the SDTV video signal and the SDTV recording OSD to generate an SDTV recording video signal and outputting the SDTV recording video signal to the SDTV recording apparatus 107.

Note that although not illustrated in FIG. 5, in the second embodiment, also, the video processor 103 includes a PIP/

POP image generating circuit such as illustrated in FIG. 1, and is connected to a non-illustrated external video device.

As in the first embodiment, the PIP/POP image generating circuit is configured so as to generate a PIP/POP image under predetermined conditions, and output an observation-related PIP/POP image or a recording-related PIP/POP image to the HDTV observation video signal synthesizing circuit 141, the HDTV recording video signal synthesizing circuit 142 or the SDTV recording video signal synthesizing circuit 143, respectively.

The HDTV observation video signal synthesizing circuit 141, the HDTV recording video signal synthesizing circuit 142 and the SDTV recording video signal synthesizing circuit 143 are configured so as to synthesize the observation-related PIP/POP image or the recording-related PIP/POP image from the PIP/POP image generating circuit with a video signal, respectively.

Furthermore, the video processor 103 includes an HDTV observation video signal output circuit 144 that outputs an HDTV observation video signal outputted from the HDTV observation video signal synthesizing circuit 141 to the HDTV observation monitor 105; an HDTV recording video signal output circuit 145 that outputs an HDTV recording video signal outputted from the HDTV recording video signal synthesizing circuit 142 to the HDTV recording apparatus 106; and an SDTV recording video signal output circuit 146 that outputs an SDTV recording video signal outputted from the SDTV recording video signal synthesizing circuit 143 to the SDTV recording apparatus 107.

Next, operation of the second embodiment will be described.

Under the control of the CPU 131 in the video processor 103, the HDTV observation OSD generating circuit 136, the HDTV recording OSD generating circuit 137 and the SDTV recording OSD generating circuit 138 output observation-related textual information or recording-related textual information relating to the respective items, ON/OFF of which is set, for example, as illustrated in FIG. 4 via operation of the keyboard 8, to the HDTV observation video signal synthesizing circuit 141, the HDTV recording video signal synthesizing circuit 142 or the SDTV recording video signal synthesizing circuit 143.

Next, under the control of the CPU 131, the HDTV observation video signal synthesizing circuit 141 provides HDTV observation-related textual information, which is observation OSD, to an HDTV video signal, which is an endoscopic image signal outputted from the post-processing circuit 135, that is, synthesizes the HDTV video signal and the HDTV observation-related textual information to generate an HDTV observation video signal and outputs the HDTV observation video signal to the HDTV observation monitor 105 via the HDTV observation video signal output circuit 144.

Here, if an observation-related PIP/POP image from the non-illustrated PIP/POP image generating circuit is inputted to the HDTV observation video signal synthesizing circuit 141, the observation-related PIP/POP image is synthesized with the video signal.

On the other hand, under the control of the CPU 131, the HDTV recording video signal synthesizing circuit 142 provides HDTV recording-related textual information, which is recording OSD, to a HDTV video signal outputted from the post-processing circuit 135, that is, synthesizes the HDTV video signal and the HDTV recording-related textual information to generate an HDTV recording video signal and outputs the HDTV recording video signal to the HDTV recording apparatus 106 via the HDTV recording video signal output circuit 145.

Here, if a recording-related PIP/POP image is inputted from the PIP/POP image generating circuit to the HDTV recording video signal synthesizing circuit 142, the recording-related PIP/POP image is synthesized with the video signal.

Furthermore, under the control of the CPU 131, the SDTV recording video signal synthesizing circuit 143 provides SDTV recording-related textual information, which is recording OSD, to an SDTV video signal outputted from the reduction circuit 148, that is, synthesizes the SDTV video signal and the SDTV recording-related textual information to generate an SDTV recording video signal and outputs the SDTV recording video signal to the SDTV recording apparatus 107 via the SDTV recording video signal output circuit 146.

Here, as in the above, if a recording-related PIP/POP image from the PIP/POP image generating circuit is inputted to the SDTV recording video signal synthesizing circuit 143, the recording-related PIP/POP image is synthesized with the video signal.

Here, in order to generate a recording video signal for HDTV with HDTV observation-related textual information provided thereto and a recording video signal for SDTV with SDTV observation-related textual information provided thereto in addition to a video signal for an observation monitor with predetermined observation OSD provided thereto as in the second embodiment, it is necessary to generate the "video signal for HDTV" and the "video signal for SDTV" in a video processor.

In order to generate the "video signal for HDTV" and the "video signal for SDTV", it is conceivable that an output signal from the magnification/reduction circuit 134 is divided and the divided signals are subjected to respective predetermined post-processing to generate a video signal for HDTV and a video signal for SDTV.

However, this configuration requires an HDTV post-processing circuit and an SDTV post-processing circuit as "post-processing circuits".

On the other hand, in the second embodiment, an output signal from the magnification/reduction circuit 134 is not divided, but the output signal (that is, the HDTV video signal) is subjected to post-processing in the post-processing circuit 135 alone, and while for the "video signal for HDTV" used in the HDTV observation video signal synthesizing circuit 141 and the HDTV recording video signal synthesizing circuit 142, the HDTV video signal subjected to the post-processing in the post-processing circuit 135 is used, the "video signal for SDTV" used in the SDTV recording video signal synthesizing circuit 143 is newly generated by reducing the HDTV video signal subjected to the post-processing in the post-processing circuit 135, in the reduction circuit 148.

In other words, in the second embodiment of the present invention, although the "video signal for HDTV" and the "video signal for SDTV" are required in order to generate the HDTV recording video signal and the SDTV recording video signal, as a so-called post-processing circuit, it is sufficient to provide only one post-processing circuit.

Furthermore, in the second embodiment according to the present invention, when the SDTV recording video signal is generated by means of synthesis such as described above, "the HDTV video signal with the HDTV observation-related textual information provided thereto" is not simply reduced, but "'the video signal for SDTV' generated by reduction of the HDTV video signal" is used as a synthesis source video signal, and OSD to be provided to the video signal is generated specially for SDTV.

As described above, according to the second embodiment of the present invention, as in the above-described first embodiment, an observation video signal of a display screen of a subject image with additional information for observation display provided thereto, and a recording video signal (HDTV recording video signal or SDTV recording video signal) of the display screen of the subject image with additional information for recording provided thereto in the same manner as above can be generated independently from each other, and thus, as in the above, for example, setting can be made so that patient data that is personal information to be displayed on the HDTV observation monitor 105 is prevented from being recorded in the HDTV recording apparatus 106 and the SDTV recording apparatus 107.

Also, in the second embodiment, although as a so-called post-processing circuit, only one post-processing circuit is provided, the "video signal for HDTV" and the "video signal for SDTV" for generating the HDTV recording video signal and the SDTV recording video signal can be prepared.

Furthermore, the second embodiment enables circuit size decrease as compared to the configuration in which an output signal from the magnification/reduction circuit 134 is divided and the divided signals are subjected to respective predetermined post-processing to generate a video signal for HDTV and a video signal for SDTV.

Furthermore, the second embodiment enables, while the circuit size is decreased, ensuring of a quality of OSD used in an SDTV recording video signal because "HDTV video signal with HDTV observation-related textual information provided thereto" is not simply reduced, but OSD to be provided to a video signal is generated specially for SDTV.

In addition, the second embodiment enables provision of OSD information for an observation monitor and OSD information for a recording apparatus, which are independent from each other.

Third Embodiment

Although in the second embodiment of the invention of the present application, as described above, a recording video signal that is independent from that for an observation monitor is generated not only for a recording apparatus that supports HDTV, but also a recording apparatus that supports SDTV, in the third embodiment, also, a recording video signal that is independent from that for an observation monitor is generated not only for a recording apparatus that supports HDTV but also a recording apparatus that supports HDTV and SDTV.

However, in the third embodiment, the SDTV recording OSD generating circuit specially provided in the second embodiment is omitted, and an SDTV recording video signal is generated using an HDTV recording video signal.

Therefore, components that are similar to those of the second embodiment will be provided with reference numerals that are similar to those of the second embodiment in the figures and detailed description thereof will be omitted here.

Figure 6:
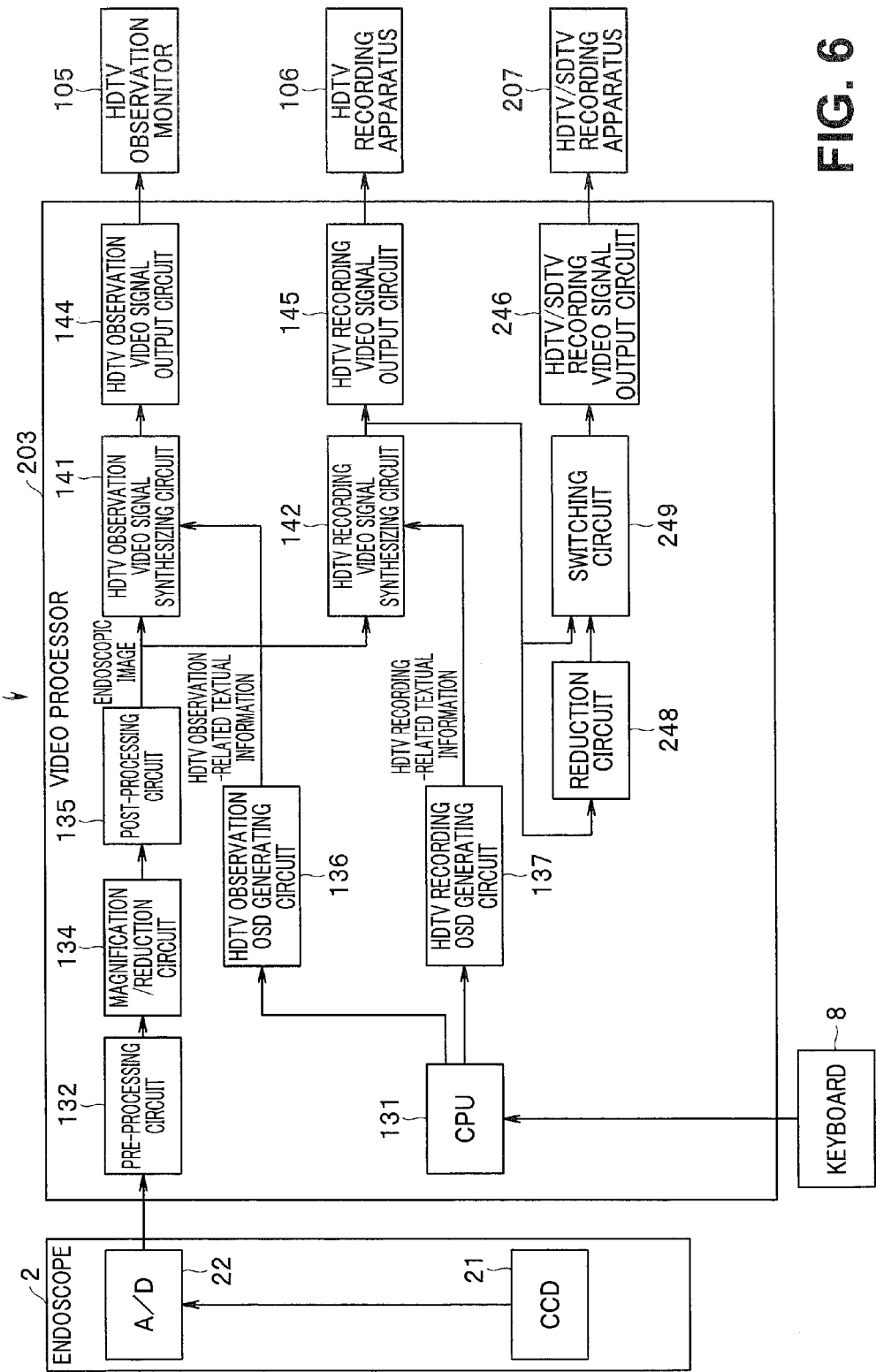
FIG. 6 is a diagram illustrating a configuration of a video output apparatus according to a third embodiment of the present invention.

FIG. 6 is a diagram illustrating a configuration of a video output apparatus according to a third embodiment of the present invention.

As illustrated in FIG. 6, as in the first and second embodiments, an endoscope system 201 according to a third embodiment of the present invention includes an endoscope 2 including a CCD image sensor 21, and a video processor 203 connected to the endoscope 2, the video processor 203 performing predetermined signal processing of an image pickup signal from the CCD image sensor 21 and generating a video signal that is independent from that for an observation monitor, for a recording apparatus that supports SDTV (recording apparatus that supports HDTV and SDTV in the present embodiment).

Furthermore, the endoscope system 201 according to the third embodiment mainly includes an HDTV observation monitor 105 and an HDTV recording apparatus 106, which are configured as in the second embodiment, and an HDTV/SDTV recording apparatus 207 that is independent from that for an observation monitor, the recording apparatus 207 being generated in the video processor 203 and supporting both the HDTV and SDTV, and a keyboard 8 via which predetermined operation is performed, the keyboard 8 being connected to the video processor 203.

The video processor 203 according to the third embodiment has a configuration that is basically similar to that of the video processor 103 in the second embodiment, but the SDTV recording OSD generating circuit 138 (see FIG. 5) in the video processor 103 is omitted.

Instead, the video processor 203 includes a reduction circuit 248 that receives an output signal from an HDTV recording video signal synthesizing circuit 142, that is, an HDTV recording video signal obtained by synthesizing HDTV recording-related textual information with an HDTV video signal, and reduces the signal to generate an SDTV recording video signal.

The video processor 203 also includes a switching circuit 249 that switches between the "SDTV recording video signal" from the reduction circuit 248 and the "HDTV recording video signal" from the HDTV recording video signal synthesizing circuit 142 and outputs the resulting signal.

The video processor 203 further includes an HDTV/SDTV recording video signal output circuit 246 that outputs the "SDTV recording video signal" or the "HDTV recording video signal" resulting from the switching via the switching circuit 249, to the HDTV/SDTV recording apparatus 207.

The rest of the configuration is similar to that of the second embodiment and thus description thereof will be omitted here.

Next, operation of the third embodiment will be described.

Under the control of a CPU 131 in the video processor 203, as in the second embodiment, the HDTV observation OSD generating circuit 136 and an HDTV recording OSD generating circuit 137 output observation-related textual information or recording-related textual information relating to the respective items, ON/OFF of which is set, for example, as illustrated in FIG. 4 via operation of the keyboard 8, to an HDTV observation video signal synthesizing circuit 141 or the HDTV recording video signal synthesizing circuit 142.

Next, as in the second embodiment, the HDTV observation video signal synthesizing circuit 141 synthesizes an HDTV video signal and HDTV observation-related textual information to generate an HDTV observation video signal, and outputs the HDTV observation video signal to the HDTV observation monitor 105 via an HDTV observation video signal output circuit 144.

Also, as in the second embodiment, the HDTV recording video signal synthesizing circuit 142 synthesizes an HDTV video signal and HDTV recording-related textual information to generate an HDTV recording video signal, and outputs the HDTV recording video signal to the HDTV recording apparatus 106 via an HDTV recording video signal output circuit 145.

Then, in the third embodiment, under the control of the CPU 131, the video processor 203 switches between an "SDTV recording video signal" from the reduction circuit 248 and the "HDTV recording video signal" from the HDTV recording video signal synthesizing circuit 142 via the switching circuit 249, and outputs the resulting signal.

Subsequently, the video processor 203 outputs the "SDTV recording video signal" or the "HDTV recording video signal" resulting from the switching via the switching circuit 249 to the HDTV/SDTV recording apparatus 207 via an HDTV/SDTV recording video signal output circuit 246.

As described above, the third embodiment of the present invention enables integration of a video signal output pathway for HDTV recording and a video signal output pathway for SDTV recording into a single output system in addition to provision of effects that are similar to those of the above-described first embodiment.

Note that although in the present embodiments, a CCD image sensor is employed for the image pickup device in the endoscope 1, the image pickup device in the present invention is not limited to this, and obviously, a video output apparatus according to the present invention may be a video output apparatus that subjects an image pickup signal from an endoscope using another image pickup device such as a CMOS sensor to predetermined image processing.

Furthermore, although in the above-described embodiments, a video processor in an endoscope system is taken as an example of a video output apparatus, a video output apparatus according to the present invention is not limited to this, and the present invention is applicable to, for example, a video output apparatus that processes an image that is not an endoscopic image, such as a video camera.

Note that the present invention is not limited to the above-described embodiments as they are, and, in the practical phase, can be embodied with components modified without departing from the spirit of the invention. Also, various aspects of the invention can be formed by arbitrary combinations of a plurality of components disclosed in the above embodiments. For example, some components may be removed from all the components indicated in an embodiment. Furthermore, components in different embodiments may arbitrarily be combined.

As described above, obviously, various modifications and applications are possible without departing from the spirit of the invention.

What is claimed is:

1. A video output apparatus comprising:
    a video signal processing section that subjects an image pickup signal obtained by picking up an image of a subject to image processing to generate a first video signal representing an image having a first resolution;
    a first text superimposing section that superimposes first textual information on the first video signal;
    a first output section that outputs the first video signal with the first textual information superimposed;
    a reduction processing section that receives the first video signal outputted from the video signal processing section, and subjects the received video signal to reduction processing to generate a second video signal representing an image having a second resolution that is lower than the first resolution;
    a second text superimposing section that superimposes second textual information on the second video signal; and
    a second output section that outputs the second video signal with the second textual information superimposed.

2. The video output apparatus according to claim 1, further comprising an additional information setting section that sets textual information to be superimposed in the first and second text superimposing sections individually.

3. The video output apparatus according to claim 1, wherein the video signal processing section subjects the image pickup signal obtained by an image pickup device provided in an endoscope picking up an image of an inside of the subject, to the image processing.

4. The video output apparatus according to claim 2, wherein:
    the first textual information and the second textual information include a plurality of items in common with each other; and
    the additional information setting section is capable of setting an item to be provided to the video signal as the second textual information, from among the items in common with each other.

5. The video output apparatus according to claim 1, wherein:
    the first video signal is a video signal in an HDTV format; and
    the second video signal is a video signal in an SDTV format.

\* \* \* \* \*